(12) United States Patent
Cunliffe et al.

(10) Patent No.: US 12,285,309 B2
(45) Date of Patent: Apr. 29, 2025

(54) METHODS TO AUTOMATICALLY REMOVE COLLISIONS BETWEEN DIGITAL MESH OBJECTS AND SMOOTHLY MOVE MESH OBJECTS BETWEEN SPATIAL ARRANGEMENTS

(71) Applicant: Solventum Intellectual Properties Company, Maplewood, MN (US)

(72) Inventors: Alexandra R. Cunliffe, St. Paul, MN (US); Benjamin D. Zimmer, Hudson, WI (US); Guruprasad Somasundaram, Woodbury, MN (US); Deepti Pachauri, Minneapolis, MN (US); Jonathan D. Gandrud, Woodbury, MN (US); Arash Sangari, Frisco, TX (US); Shawna L. Thomas, College Station, TX (US); Nancy M. Amato, Champaign, IL (US)

(73) Assignee: Solventum Intellectual Properties Company, Maplewood, MN (US)

( * ) Notice: Subject to any disclaimer, the term of this patent is extended or adjusted under 35 U.S.C. 154(b) by 568 days.

(21) Appl. No.: 17/413,652

(22) PCT Filed: Dec. 24, 2019

(86) PCT No.: PCT/IB2019/061347
§ 371 (c)(1),
(2) Date: Jun. 14, 2021

(87) PCT Pub. No.: WO2020/136587
PCT Pub. Date: Jul. 2, 2020

(65) Prior Publication Data
US 2022/0054234 A1 Feb. 24, 2022

Related U.S. Application Data

(60) Provisional application No. 62/784,968, filed on Dec. 26, 2018.

(51) Int. Cl.
*A61C 7/00* (2006.01)
*G16H 20/00* (2018.01)
*G16H 50/50* (2018.01)

(52) U.S. Cl.
CPC ............ *A61C 7/002* (2013.01); *G16H 20/00* (2018.01); *G16H 50/50* (2018.01)

(58) Field of Classification Search
CPC .......... A61C 7/002; A61B 34/10; A61B 6/14; G16H 50/50; G06F 17/50
See application file for complete search history.

(56) References Cited

U.S. PATENT DOCUMENTS

| 7,605,817 | B2 | 10/2009 | Zhang |
| 7,956,862 | B2 | 6/2011 | Zhang |

(Continued)

FOREIGN PATENT DOCUMENTS

| WO | WO 98-058596 | 12/1998 |
| WO | 2006118771 A2 | 11/2006 |
| WO | WO 2019-069191 | 4/2019 |

OTHER PUBLICATIONS

Kumar, "Automatic Virtual Alignment of Dental Arches in Orthodontics," Computer-Aided Design and Applications, 2013, vol. 10, No. 3, pp. 371-398.

(Continued)

*Primary Examiner* — Nicholas D Lucchesi (57) ABSTRACT

Methods for automatically removing collisions between digital mesh objects and moving digital mesh objects between spatial arrangements. The collisions are removed from a set of digital mesh objects using a perturbation method or a mesh deformation method. After removing the collisions, the digital mesh objects are output in a state without collisions between them. The digital mesh objects can be moved between initial and final states based upon motion constraints of the mesh objects and interpolated (Continued)

states of them between the initial and final states. Based upon the constraints and interpolated states, a number of states for movement of the set of digital mesh objects is determined either collectively for the set or individually for each mesh object. The states can be used as digital setups for dental or orthodontic treatment planning.

20 Claims, 8 Drawing Sheets

(56) References Cited

U.S. PATENT DOCUMENTS

| | | | | |
|---|---|---|---|---|
| 9,161,824 | B2* | 10/2015 | Chishti | A61C 7/00 |
| 9,211,166 | B2* | 12/2015 | Kuo | G06F 30/20 |
| 9,439,608 | B2* | 9/2016 | Schutyser | A61B 5/1077 |
| 9,848,958 | B2* | 12/2017 | Matov | A61C 7/002 |
| 9,922,454 | B2* | 3/2018 | Jaisson | A61C 7/002 |
| 10,548,690 | B2* | 2/2020 | Wen | G16H 30/20 |
| 10,624,717 | B2* | 4/2020 | Wen | G06T 11/60 |
| 11,259,896 | B2* | 3/2022 | Matov | A61C 7/08 |
| 11,495,003 | B1* | 11/2022 | Agarwal | G06F 3/016 |
| 2003/0080957 | A1 | 5/2003 | Stewart | |
| 2005/0055118 | A1 | 3/2005 | Nikolskiy | |
| 2008/0182220 | A1 | 7/2008 | Chishti et al. | |
| 2008/0261165 | A1 | 10/2008 | Steingart | |
| 2013/0066598 | A1 | 3/2013 | Fisker | |
| 2013/0317800 | A1 | 11/2013 | Wu | |
| 2017/0100207 | A1 | 4/2017 | Wen | |
| 2020/0214801 | A1* | 7/2020 | Wang | G06F 30/20 |
| 2020/0229900 | A1* | 7/2020 | Cunliffe | A61C 7/002 |
| 2021/0259808 | A1* | 8/2021 | Ben-Gal Nguyen | G06N 3/088 |
| 2022/0160469 | A1* | 5/2022 | Cunliffe | G16H 20/40 |

OTHER PUBLICATIONS

International Search report for PCT International Application No. PCT/IB2019/061347 mailed on Apr. 21, 2020, 4 pages.
Extended European Search Report, EP19906569.9, Aug. 8, 2022, 3 pages.

* cited by examiner

METHODS TO AUTOMATICALLY REMOVE COLLISIONS BETWEEN DIGITAL MESH OBJECTS AND SMOOTHLY MOVE MESH OBJECTS BETWEEN SPATIAL ARRANGEMENTS

CROSS REFERENCE TO RELATED APPLICATIONS

This application is a national stage filing under 35 U.S.C. 371 of PCT/IB2019/061347, filed Dec. 24, 2019, which claims the benefit of U.S. Provisional Application No. 62/784,968, filed Dec. 26, 2018, the disclosures of which are incorporated by reference in their entireties herein.

BACKGROUND

The objective of an orthodontic treatment planning process is to create a set of valid states that teeth can move between in order to achieve an orthodontically correct final setup. Those states can then be used to design clear tray aligners or other orthodontic appliances. Constraints-based motion between states is a necessary first step in the planning process, as it creates an approximate path that teeth with take between an initial and final setup. It may also be used by a technician in an interactive software system to design a treatment plan or used in a doctor's office to show the patient an approximation of tooth movement during treatment. Subsequent refinement, however, would likely be required in order to remove collisions between teeth in the interpolated path. A need exists to automatically remove collisions among the states and create a smooth movement path between the states for orthodontic treatment planning or other purposes.

SUMMARY

A first method for automatically removing collisions between digital mesh objects includes receiving a set of digital mesh objects in a first state with one or more collisions between the digital mesh objects, removing the collisions using a perturbation method, and outputting a set of transformations describing tooth movement between the first state and a second state or tooth positions in the second state.

A second method for automatically removing collisions between digital mesh objects includes receiving a set of digital mesh objects in a first state with one or more collisions between the digital mesh objects, removing the collisions using a mesh deformation method, and outputting the set of digital mesh objects in a second state without collisions between them.

A method for moving digital mesh objects between spatial arrangements includes receiving a set of digital mesh objects in an initial state and receiving a final state for the set of digital mesh objects. The method also includes identifying motion constraints among the digital mesh objects, estimating a number of interpolated states (n) of the digital mesh objects between the initial and final states based upon the constraints, and creating n number of interpolated states for movement of the set of digital mesh objects between the initial and final states.

The states of the digital mesh objects can be used as digital setups for dental or orthodontic treatment planning.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Embodiments include automated methods to remove collisions between digital mesh objects and smoothly move digital mesh objects between different spatial arrangements. The methods can be used, for example, to generate digital setups for use in dental or orthodontic treatment planning. The methods can also be used with other collections of digital mesh objects in other applications of them.

Methods to automatically generate digital setups for orthodontic appliances are described in U.S. Provisional Patent Application Ser. No. 62/569,081, entitled "Automated Process for Intermediate Orthodontic Digital Setup Generation," and filed Oct. 6, 2017, which is incorporated herein by reference as if fully set forth.

Figure 1:
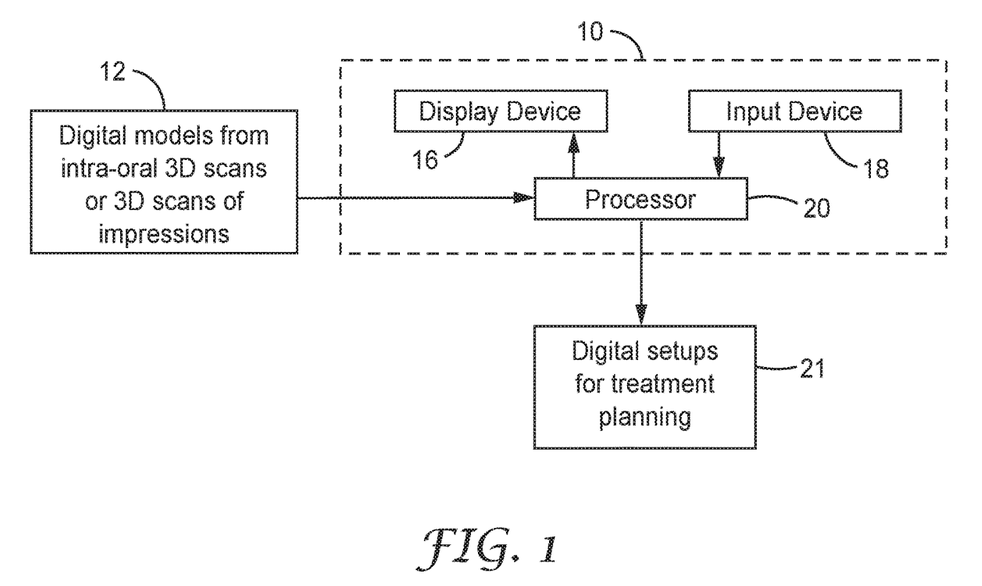
FIG. 1 is a diagram of a system 10 for removing collisions between digital mesh objects and smoothly move digital mesh objects between spatial arrangements for dental or orthodontic treatment planning.

FIG. 1 is a diagram of a system 10 for removing collisions between digital mesh objects and smoothly move digital mesh objects between spatial arrangements for dental or orthodontic treatment planning. System 10 includes a processor 20 receiving digital 3D models of teeth (12) from intra-oral 3D scans or scans of impressions of teeth, or in other embodiments the system receives user manual input. System 10 can also include an electronic display device 16, such as a liquid crystal display (LCD) device, and an input device 18 for receiving user commands or other information. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth and gingiva. System 10 can be implemented with, for example, a desktop, notebook, or tablet computer. System 10 can receive the 3D scans locally or remotely via a network.

The 3D scans addressed herein are represented as triangular meshes. The triangular mesh is a common representation of 3D surfaces and has two components. The first component, referred to as the vertices of the mesh, are simply the coordinates of the 3D points that have been reconstructed on the surface—i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

The methods and algorithms described herein can be implemented, for example, in software or firmware for execution by a processor such as processor 20.

Automatically Removing Collisions Between Mesh Objects

Described herein are methods that can be used to remove collisions between a set of digital mesh objects, either by perturbing the objects in directions that are likely to remove collisions, or by deforming the shape of the mesh objects. The term digital mesh objects includes mesh objects. A list of the discussed methods and brief description of each method are presented in Tables 1 and 2 below.

TABLE 1

| Methods to remove collisions through intelligent perturbation | Methods to remove collisions through mesh deformation |
| --- | --- |
| Directional perturbation | Local mesh deformation at colliding surfaces |
| Propagated directional perturbation | Global mesh shrinking |
| Gradient descent | |
| Simultaneous perturbation stochastic approximation (SPSA) | |
| Grid search | |
| Behavior mode-based perturbation | |
| Genetic algorithm | |

TABLE 2

| Directional perturbation | Derive a direction vector in which to perturb teeth that are in collision |
| --- | --- |
| Propagated directional perturbation | Derive a direction vector in which to perturb teeth that are in collision and neighboring teeth |
| Gradient descent | Exploration of a space of possible perturbation directions according to an objective function |
| Simultaneous perturbation stochastic approximation (SPSA) | Exploration of a space of possible perturbation directions according to an objective function |
| Grid search | Explore the space of possible perturbation directions by systematically varying model parameters |
| Behavior mode-based perturbation | Move teeth according to higher level rules about orthodontic treatment |
| Genetic algorithm | Explore the space of possible solutions using evolution |
| Local mesh deformation at colliding surfaces | Move mesh vertices that are in collision |
| Global mesh shrinking | Globally shrink teeth that are in collision |

Also discussed herein are interactive tools that can be used in an orthodontic treatment planning setting to automatically remove collisions between teeth using these methods.

The description of the methods is divided into two sections. The first section presents a set of intelligent perturbation functions that can be used to shift one or more mesh objects in order to remove collisions without changing their shape. These functions could be applied to remove collisions between a set of teeth without modifying the shape of the tooth mesh. The second section presents techniques that can be used to deform the shape of the mesh objects themselves to remove collisions without shifting their locations. This could be applied to remove collisions between teeth that are falsely in collision due to scanner artifacts. Each approach may be necessary for different parts of the treatment planning process. For example, perturbation may be desirable when attempting to discover a collision-free trajectory between states, whereas mesh deformation may be desirable if collisions are introduced due to artifacts in the mesh that are not present in actual tooth anatomy.

Figure 2:
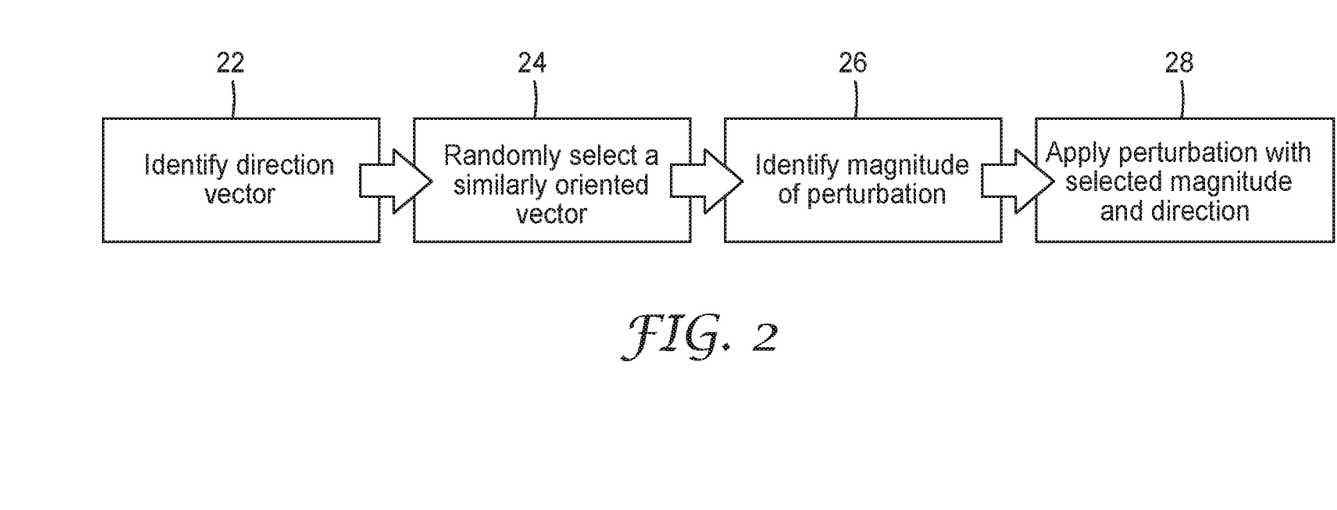
FIG. 2 is a flow chart of a method to automatically remove collisions between mesh objects.

Section 1: Methods to Automatically Remove Collisions Using Intelligent Perturbation Functions I. Directional Perturbation For this approach, an advantageous direction that a mesh or collection of mesh objects are perturbed towards is identified, and the one or more objects are perturbed in this general direction. A flow chart of this approach is shown in FIG. 2.

First, for each object, an advantageous direction, defined as a vector in three-dimensional space, is identified (step 22). This information could either be input by a user or computed based on information such as the vector opposite the penetration between the objects (Method A), the vector perpendicular to the penetration between objects (Method B), or the vector of motion towards an ideal state that does not contain any collisions or contains fewer collisions (Method C). In the next optional step, a vector that is no more than an angle theta from the identified direction is randomly selected for each object (step 24). This optional step provides an element of randomness to the approach that would allow the algorithm to search a space nearby the selected direction for the optimal solution. Next, the magnitude of the perturbation is identified for each object (step 26). The magnitude(s) may be chosen either entirely randomly, through user input, or using some information (e.g., the penetration depth) to define the amount of perturbation, or as a scale factor on the perturbation amount. In the final step, the perturbation is applied to the mesh object(s) by shifting the object(s) by the specified magnitude(s) along their respective vector(s) (step 28).

Method A: Compute the Direction of Penetration (and Penetration Depth) Between Two Objects Aspects of this approach are also referenced in Section 2, Method 1. First, principle component analysis (PCA) is used to fit contact points between two colliding objects to a plane. Other methods for plane fit such as support vector regression can also be used. The penetration direction is identified as the direction normal to the plane (e.g., the vector associated with the smallest principle component), or alternatively, as the mean of the vertex normal directions for all contact points. Penetration depth may also be computed by identifying the vertices that lie within the boundary formed by the contact points (see Section 2, Method 1), then computing the maximum point-to-plane distance when vertices are projected onto the plane along the penetration direction. The sum of the maximum point-to-plane distances for the two colliding objects is the penetration depth.

Method B: Compute the Direction Perpendicular to the Direction of Penetration Between Two Objects The direction perpendicular to the penetration direction may also be computed through PCA or using the plane equation once the plane is computed. Specifically, the vectors associated with the two largest principle components are two directions that are perpendicular to the penetration direction. More generally, the vectors perpendicular to the penetration direction lie on a plane, and any of the vectors may be chosen as the perpendicular direction.

Method C: Compute the Direction Towards an Ideal State

In the case that an ideal state that is either collision-free or contains fewer collisions is available, the perturbation direction vector for each object towards this ideal state may be computed as:

$$\frac{(\Delta x, \Delta y, \Delta z)}{\|(\Delta x, \Delta y, \Delta z)\|}$$

II. Propagated Direction Perturbation

In additional to the objects that are in collision, neighboring objects may also be moved using the perturbation function described above. Perturbing non-colliding objects that are nearby colliding objects has the advantage of creating space for the colliding objects to move into without creating new collisions. The method to perturb colliding mesh objects and their neighbors is similar to the method described above. First, a set of mesh objects that are in the local neighborhood of the colliding objects is identified. Next, the perturbation direction for each object is identified using one of the methods described above (Method A, B, or C). To minimize unnecessary motion, it may be desirable to set the magnitude of perturbation for each object to a value less than or equal to the magnitude identified for the colliding objects. One option to achieve this outcome is to scale the magnitude of perturbation according to the distance between the colliding objects and the neighboring objects, such that objects that are closer to the colliding objects have larger magnitudes, while objects farther from the colliding objects have smaller magnitudes.

III. Gradient Descent

The validity of each point of the trajectory is evaluated using a scoring function, which penalizes teeth collisions. Whenever there is no collision between teeth, this scoring function returns zero, and the score increases with collisions. The gradient descent method finds optimal tooth motion by perturbing their corresponding states in a way that the collision score reduces.

The problem of finding the optimal perturbation that reduces the score function, is a complex nonlinear optimization problem. Although there is no guarantee for finding a global solution, deepest descent methods can be used to find the optimal direction for perturbing states that reduces the collision score to a local minimum.

Since calculating the collision points between the complex geometries such as teeth cannot be represented in a closed mathematical form, the gradient of the score function with respect to object motions should be numerically approximated. To calculate an approximation of gradient, each state can be perturbed many times so that the rate of change of the score with respect to each state can be calculated. The rate of change of the score (i.e., gradient of an objective function) is used to derive a direction vector in which to ultimately move the objects.

First, a subset of the objects in the state are identified by selecting objects that are in collision as well as adjacent objects. For each degree of freedom (or each degree of freedom corresponding to translation) in the degree of freedom vector of each object, the change in the objective function when adding and subtracting a small delta to that degree of freedom is recorded. The resulting vector of changes is normalized and treated as an estimate of the direction of the gradient of the objective function. To create a random perturbation of a state, the negative of the gradient multiplied by a scaling factor is added to the degrees of freedom vectors of the state, along with a small random component. The scaling factor is a random number between 0 and a maximum estimated using the penetration depths of the state.

IV. Simultaneous Perturbation Stochastic Approximation (SPSA)

An alternative method for approximating gradient is called Simultaneous Perturbation Stochastic Approximation (SPSA). In order to approximate the deepest descent direction using SPSA, one can choose a random direction to perturb the current state and calculate the rate of change of the score along that random direction. The main benefit of SPSA method is that in order to have an approximation of the perturbation direction, only two function calls of the score function are enough. In comparison, the numerical gradient approximation requires 2n functions call, where n is the dimension of the state vectors. For the cases that calling the score function is computationally costly, SPSA may result a faster convergence time, since a rough approximation of the deepest descent direction can rapidly progress the optimization toward better regions. Augmenting SPSA with a momentum technique can also keep track of the history of the estimated directions for a more accurate deepest descent result. In the following section, SPSA method is described in more detail.

Approximating the Steepest Descent Direction Using SPSA:

If one considers $f(\ )$ as a scoring function, and $x = [x_1, x_2, \ldots x_n]$ as the current state, the random direction $\Delta = [\Delta_1, \Delta_2, \ldots \Delta_n]$ and the fixed perturbation size c can be used to calculate SPSA of the gradient of (x), that is denoted by g(x):

$$g(x) = \begin{bmatrix} \frac{f(x+c\Delta) - f(x-c\Delta)}{2c\Delta_1} \\ \vdots \\ \frac{f(x+c\Delta) - f(x-c\Delta)}{2c\Delta_n} \end{bmatrix}$$

In order to avoid numerical instability of calculating g(x), each element of $\Delta$ is sampled from a uniform Bernoulli distribution $$\Delta_t \sim Ber_{1/2}\left\{\frac{-1}{\sqrt{n}}, \frac{1}{\sqrt{n}}\right\}.$$

Therefore, the perturbation direction vector $\Delta$ is a unit norm. In the above definition, the magnitude of the perturbation can be controlled by the perturbation size variable c.

Steepest Descent Optimization Using SPSA:

Let the initial state be denoted by x(0), the approximation of the steepest descent using the SPSA method would be g(x(0)). Therefore, the intelligent perturbation to reduce the score can be calculated by:

$$x(1) = x(0) - \mu g(x(0)),$$

where $\mu$ is the stepsize of the steepest descent. A sequential steepest descent updating method can be used to find a local minima of the score function. In general, at any step x(i) the updated state x(i+1) can be calculated as $$x(i+1) = x(i) - \mu_i g(x(i)),$$

where $\mu_i$ is the stepsize at the i-th iteration. Decreasing the stepsize $\mu_i$ during the sequential steepest descent results in a more stable solution, for example $\mu_i=\mu/n$, where $\mu$ is the initial stepsize.

Aggregating the History of SPSA Steepest Descent Using a Momentum Method:

Since at each instance of time the SPSA steepest descent encodes the rate of change of the score function along a random direction, the path toward the local minima might be very noisy. The momentum method is a common method for keeping a history of the more recent steepest descent directions for smoothing the steepest descent direction. The momentum direction is the weighted sum of the previously calculated directions where the older directions are receiving lower weight, comparing to the more recent directions. The following equations represent the smoothed direction at the i-th iteration, go, calculated using the momentum method $$\tilde{g}(i)=g(x(i))+w\tilde{g}(i-1),$$

where w<1 is the momentum weight, and in this method its value is 0.9.

V. Grid Search Perturbation

This method performs perturbation by identifying mesh objects that need to be perturbed first using a penetration evaluator, as described earlier in the directed perturbation method. Additionally, neighboring objects can also be added to this list of possible objects that can be perturbed.

The perturbation itself is done by sequentially changing the state of the set of objects, in order to move the objects towards a higher scoring state. For each object, a spatial grid of possible locations is constructed around the object location with a predetermined spatial resolution (e.g. 1 mm). As an option, some locations can be ruled out using the penetration evaluator to speed-up the search. Then by moving each object to one of the object's own grid locations, the collision scores can be evaluated. If there are 3 objects and 9 locations for each object, that provides 729 configurations to evaluate. The best scoring configuration is chosen and then this process can be repeated over several iterations as computationally allowed each time reducing the spatial resolution of the grid by a predetermined fraction, for example 0.5. The spatial grid can be constructed in Cartesian coordinates or (for tooth data) archform coordinates. Table 3 provides exemplary pseudocode for implementing this method.

TABLE 3

Pseudocode for Grid Search Perturbation
1) Determine the objects that need to be moved
   (objects in collision + n nearest neighboring objects)
2) for each iteration (after first iteration reduce resolution)
3) for each object that needs to be moved
4) create grid spatial grid location using resolution chosen
   (optional: remove infeasible grid locations)
5) evaluate all configurations
6) select best scoring configuration as state to perturb to -
   reiterate go to step (2)

VI. Behavior Mode-Based Perturbation

Some perturb methods could derive higher-level information about the arrangement of mesh objects to choose modes of behavior. For example, if a perturb function detects that an object is in collision with both of its neighbors, it could attempt to create space by flaring those objects through motions that are perpendicular to the penetration directions. These perturb methods might not produce states that immediately improve the value of an objective function, but such states might be critical to producing a path around problem areas.

VII. Genetic Algorithm

Figure 3:
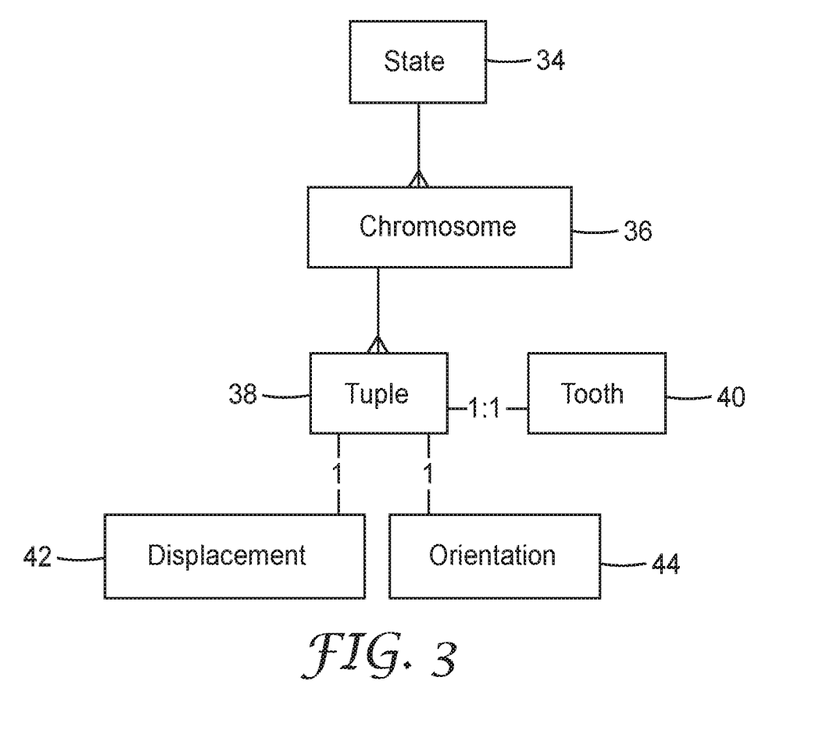
FIG. 3 is a diagram of a data model used by a genetic algorithm.

Described herein is a genetic algorithm (GA) to resolve the collisions for each state (set of teeth). FIG. 3 is a diagram of a data model used by the GA. The GA starts over for each state 34. A GA evolves a population of N chromosomes 36 (solutions) over many iterations (generations), keeping the chromosomes that exhibit high fitness (designated as parents) and deleting the chromosome with low fitness (inferiors). The parents reproduce themselves, and through mutation and crossover operations produce children that pass their successful attributes to the next generation. Evolution proceeds until a criterion is met. In this case, the method ends evolution of an intermediate setup when the method discovers a state which resolves all collisions in that intermediate setup.

Table 4 includes exemplary pseudocode for implementing the GA with the following definitions. A chromosome is a vector of tuples 38, one for each tooth 40, where each tuple 38 consists of a position modifier 42 and an orientation modifier 44.

TABLE 4

Pseudocode for Overall Genetic Algorithm

1. Generate population of N chromosomes
2. Until Done:
   a. Fitness Determination: determine population fitness
   b. Selection: Apply selection operator to choose which chromosomes get to
      reproduce (parents) and which chromosomes are selected for removal (inferiors)
   c. Mutation and Crossover: Breed the parents and use resulting children to replace
      the inferiors
Fitness Determination [this function is original]
   For each chromosome:
      For each tuple in chromosome:
         Apply tuple to its tooth
      Use Fitness Function to determine fitness of chromosome
Selection (variations are possible)
   Randomly order the chromosomes
   Group the chromosomes in groups of 4
   Remove the two lowest fitness chromosomes from each foursome
   Replace the lowest fitness chromosomes with copies of the parents
   Apply mutation and (optionally) crossover operations to the copies of the parents
Mutation
   Randomly choose one or more tuples in the chromosome. Change either the displacement
   or orientation component of that tuple by a small random amount. The algorithm accounts TABLE 4-continued Pseudocode for Overall Genetic Algorithm for constraints on tooth movement by limiting the magnitude of displacement and orientation.
Crossover
   Choose a random index inside the pair of chromosomes. Swap the tuples that appear before (or after) this index, producing two new chromosomes.
Done Criterion
   The algorithm is done when one or more of the chromosomes in the population achieves a target fitness. In this case, the algorithm requires a fitness of zero collisions.

Simple Example

Figure 4:
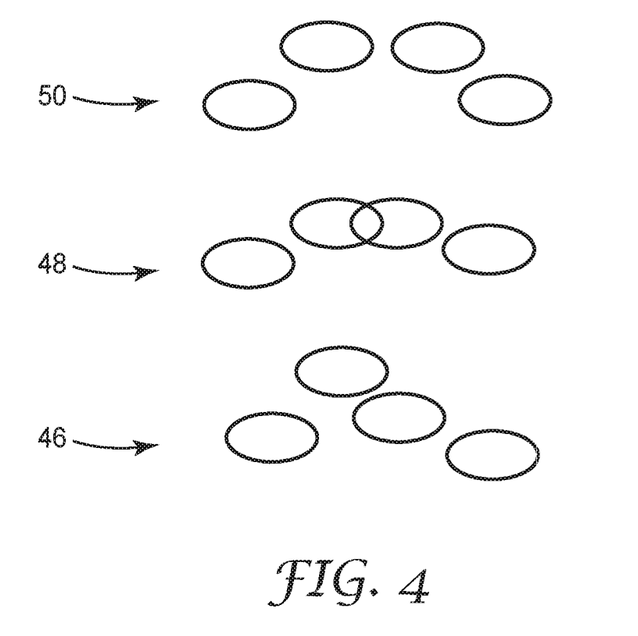
FIG. 4 is a diagram illustrating an example of an initial setup and corresponding intermediate and final setups.

FIG. 4 shows a simple example, illustrating the initial setup 46 (malocclusion), an example of one intermediate setup 48, and the final setup 50 for a simplified arch of 4 teeth. The GA is run on this intermediate state in order to resolve the collision (see the middle two ellipses in setup 48). In this case, the algorithm might create a population of N=100 chromosomes, where each chromosome comprises a vector of tuples, where each tuple comprises a small displacement and a small change in orientation (e.g., <0.04 mm, 0.09 mm, 0.01 mm>; 1.5 degrees along a given axis). The algorithm iterates the following for as many generations as necessary in order to produce a chromosome without collisions: A) measure the fitness of each chromosome (e.g., as a count of collisions), B) shuffle the population into groups of four and flag to the two lowest-fitness chromosomes for deletion, and C) replace the inferior chromosomes with copies of the parents that have undergone crossover and mutation. Iterate until done. Eventually, after many generations, the teeth in the intermediate state have been moved such that the teeth no longer have collisions. Then the process is restarted, using the next intermediate setup as input.

Interactive Tools for Orthodontic Treatment Planning from Perturb Methods

In addition to applications in algorithms that automatically remove collisions in a series of mouth states, methods that perturb teeth toward a more valid state have many potential applications in interactive tools for orthodontic treatment planning, including interactively generating intermediate and final setups, and for dental treatment planning, including planning optimal placement of an implant.

In preparing a specific arrangement of teeth for orthodontic treatment, a technician may be trying to achieve certain qualities, such as aesthetic appearance or directives from an orthodontist. However, it may be difficult to manually manipulate teeth at a small scale, so these goals are satisfied without creating collisions between the teeth. Even if the treatment planning software does not allow the teeth to be moved into collision, extra work may be required to manipulate teeth (either one at a time or in groups) into the desired state without creating collisions.

An interactive tool that allowed a perturb function to be applied to reduce or eliminate small collisions would allow the technician to focus less on collisions and more about other goals. The technician could place teeth into a state that satisfies their high-level goals but has collisions, and use the tool to find an extremely similar state that does not have collisions.

Many perturb functions described above rely on scale factors that place bounds on the distance from the original state to the perturbed state. These scale factors could be linked to sliders or other controls in a graphical user interface that allow the technician to control how extreme the motions of the teeth are as collisions are resolved.

Embodiments of this invention could also be applied in a dentistry setting to enable automated or semi-automated planning of the location of a crown, bridge, or implant. In this application, a dentist could roughly place an implant in a digital arch form such that it achieves general aesthetic goals. Intelligent perturbation functions could then be used to automatically minimize or removing both collisions between teeth on a single arch and collisions between teeth on opposite arches. Mesh deformations (described in the next section) could also be applied to the implant in order to design an implant that fits correctly in a patient's mouth. As an alternative to collisions, another score such as penetration depth or number of colliding points could also be used.

Section 2: Methods to Automatically Remove Collisions Through Mesh Deformation

Various parts of the digital orthodontic workflow may produce valid arrangements of teeth that contain collisions. There are two main causes for these collisions. First, while the teeth in their maloccluded state will not contain collisions, related geometry (such as roots) with collisions may be automatically generated. Second, technicians may intentionally create arrangements of teeth with small collisions between teeth or roots. Their rationale is that these collisions are between portions of the mesh that may represent scanning issues or segmentation errors, so they should be disregarded.

Since the various processes that optimize arrangements of teeth assess validity by checking for collisions between teeth, such collisions (especially in the final setup) are problematic. However, automatic methods may be used to eliminate collisions by modifying the geometry. These methods could also be applied interactively so that technician could confirm that the modifications to the geometry are not too extreme or are only applied to regions or objects that the technician selects.

Method 1: Automatically Remove Collisions Between Meshes Through Local Mesh Deformation Described herein is an iterative approach for collision removal whereby the portions of mesh objects that are in collision are identified and shifted until collisions are removed.

Figure 5:
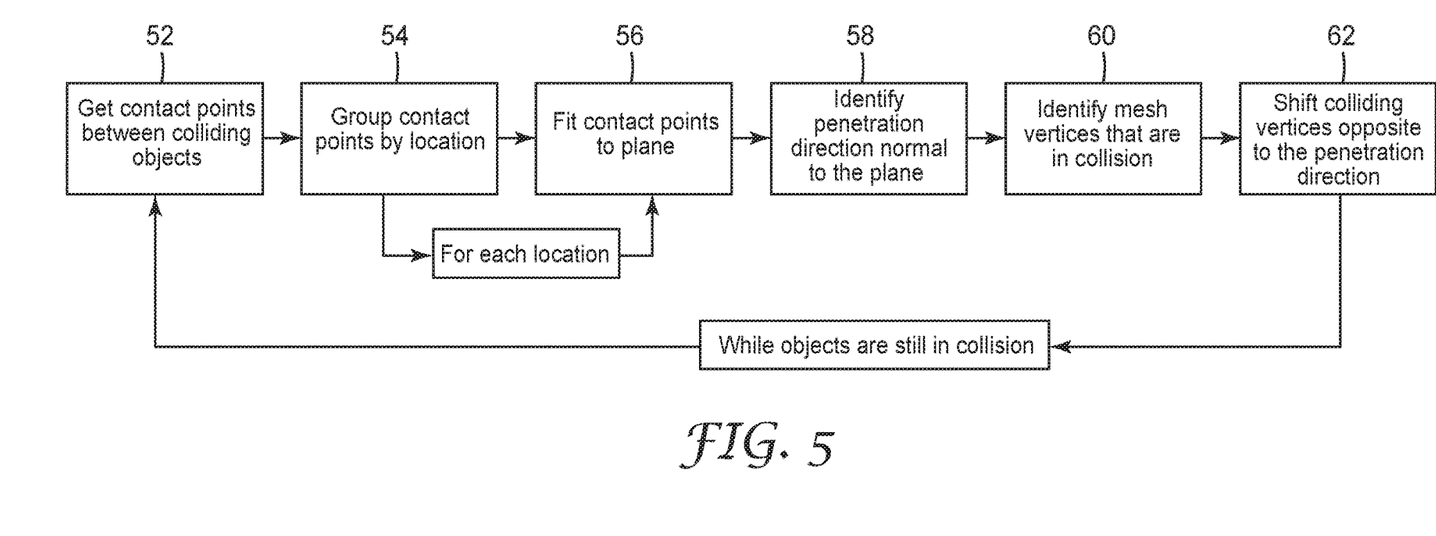
FIG. 5 is a flow chart of a method for iterative collision removal of mesh objects.
Figure 6:
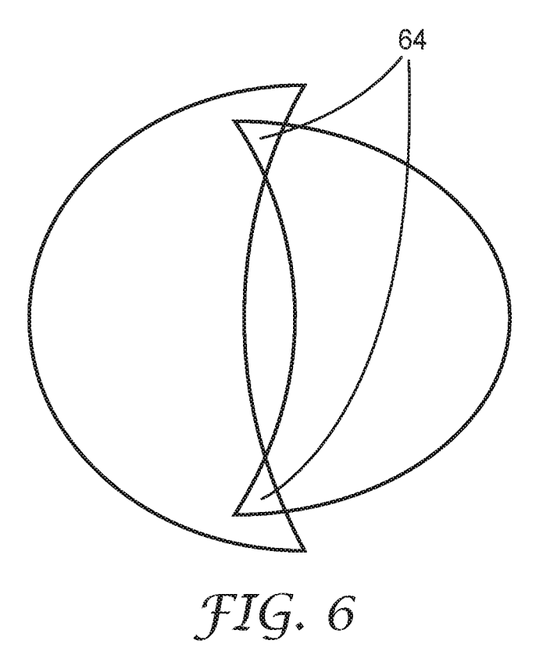
FIG. 6 is a diagram illustrating mesh objects in collision having multiple collision locations.

The process for iterative collision removal is shown in the flow chart in FIG. 5. First, the contact points between two colliding objects are identified (step 52). It is possible that objects in collision may have multiple collision locations, as illustrated in FIG. 6 showing collision locations 64. Therefore, the next step uses minimum linkage clustering to identify the contact points associated with each collision location (step 54). For each collision location, the contact points are fitted to a plane using PCA (step 56). The penetration direction may be defined either as the vector that is normal to the fitted plane (i.e., the vector associated with the smallest principle component) or the mean of the vertex normal directions at the contact points (step 58). Two ways are possible to identify mesh vertices that are in collision (step 60). In the first approach, mesh objects are cut at the plane identified by PCA, and only the sub-meshes that are closest to one another are retained. The vertices of both sub-meshes are then projected onto the plane, and vertices that are within the convex hull of the contact points are identified as being in collision. In the second approach, vertices in opposing meshes that are within a small distance, d, of each other when projected onto the plane are identified as being in collision. Colliding vertices on each mesh object are subsequently shifted by a small amount, d, in a direction opposite to the penetration direction (step 62). This process is repeated iteratively until no collisions remain between the two objects.

Method 2: Global Mesh Shrinking

Table 5 provides exemplary pseudocode for implementing a global mesh shrinking method.

TABLE 5

Pseudocode for Mesh Shrinking Algorithm

In this process, collisions in a set of meshes are removed by shrinking entire meshes:
   1. Identify which meshes are in collision.
   2. Shrink all colliding meshes by small distance d.
   3. If collisions remain, go to step 1.
To shrink a mesh by distance d:
   1. Calculate the vertex normals (unit vectors) over the whole mesh.
   2. Move each vertex in the direction opposite its normal by d.
Optionally smooth the vertices via averaging neighbors or nearby vertices.

The advantage of this method is that it preserves the overall shape of the meshes being modified and does not introduce sharp edges into previously smooth areas. However, if large shrink amounts are required to remove collisions, a large amount of error may be introduced.

This method may be better suited for automatically generated geometry, such as roots, which should retain smooth surfaces while not colliding with each other or with crown meshes.

Smoothly Moving Mesh Objects Between Spatial Arrangements

Described herein is an approach for smoothly moving a set of digital 3D mesh objects between two spatial arrangements. This method incorporates motion constraints on the per-state movement of each object, allowing for multiple objects to be moved at different rates according to their constraints. In an orthodontic treatment planning process, this constraints-based approach could be used to model tooth movement between states according to the amount of force applied to each tooth.

Orthodontic treatment planning requires moving a set of teeth from one stage to the next until arriving at the final setup. A basic approach to achieve this goal is to move teeth between stages using linear interpolation. Basic interpolation, however, assumes that all teeth move at a uniform rate, which is not the case. Rather, the amount of tooth movement for each tooth is based on the amount of force applied to the tooth (determined by the treatment appliance) and the anatomy (tooth shape, root length, jaw thickness, and others).

Figure 7:
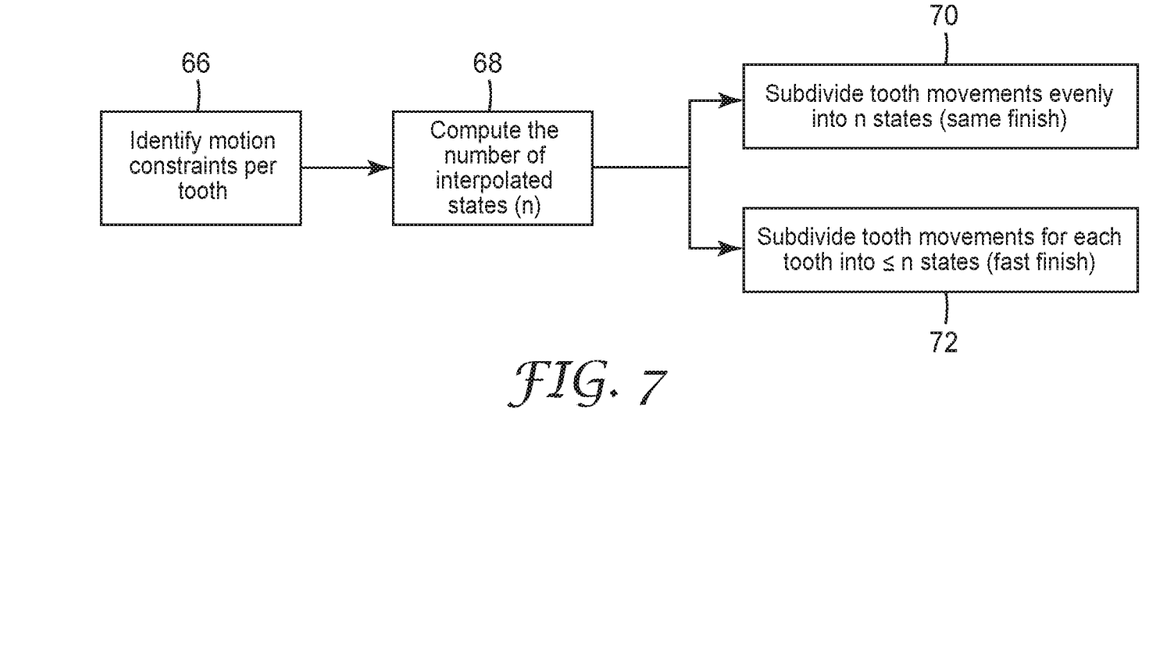
FIG. 7 is a flow chart of a method to achieve movement of teeth using a set of constraints on tooth movement.

To achieve realistic movement of teeth, one approach uses a set of constraints on tooth movement to reflect the amount of motion that is achievable on a per-tooth basis, as illustrated in the flow chart of FIG. 7.

First, the motion constraints per tooth are identified (step 66). These constraints may be provided manually by a clinician, established through heuristics, or computed using biomechanical modeling. Constraints may also be informed by other modalities such as x-ray or computed tomography (CT), which can be used to determine the root shape, root length, and jaw thickness. This information would then be combined with the treatment appliance information to determine constraints on tooth movement. Once the constraints have been established, the total number of interpolated states is estimated by subdividing total tooth movement by the constraints (steps 68). To subdivide at a higher resolution than the constraints, the constraints may be multiplied by a scale factor. Table 6 provides exemplary pseudocode for implementing these steps 66 and 68.

TABLE 6

Pseudocode for Computing Interpolated States

```
if do_high_res_interpolate:
    #reset the constraints so that interpolation is performed at a higher resolution
    constraints = constraints * scale_factor #scale factor < 1
n_translate = [ ]
n_rotate = [ ]
for tooth in teeth:
    #compute total tooth translation and rotation amount from initial to final state
    total_tooth_translation = translation_final − translation_initial
    total tooth rotation = compute_axis_angle_rotation(orientation_initial, orientation_final)
    #convert rotation amount to a value between 0 and pi
    while total_tooth rotation < 0:
        total tooth rotation = total tooth rotation + 2*pi
    while total tooth rotation > pi:
        total tooth_rotation = 2*pi − total_tooth_rotation
    #compute the number of states, n, necessary to interpolate if the method
subdivides evenly by constraints
    n_translate[tooth_i] = ceil(total_tooth_translation / tooth_translation_constraint)
    n_rotate[tooth_i] = ceil(total_tooth_rotation / tooth_rotation_constraint)
#determine the maximum number of steps
n_steps = max(max(n_translate), max(n_rotate))
#number of states is n_steps + 1
n = n_steps + 1
```

Tooth movement may be subdivided into the number of states, n, using two approaches. In the first approach ("same finish"), tooth movement is planned such that all teeth finish moving at the same time (step 70). This means that teeth with the same constraints but a different total amount of movement will move at different rates so that they finish moving at the same time. A same finish approach could be used to minimize patient discomfort during treatment. In the second approach ("fast finish"), tooth movement is planned such that each tooth finishes moving as quickly as is permitted by the constraints (step 72). This means that teeth with the same constraints but a different total amount of required movement will move at the same rate and finish moving at different times. A fast finish approach could be used to improve aesthetic appearance more quickly during treatment.

Same Finish:

Tooth translation is subdivided into the number of states, n, by dividing the total translation amount evenly among the states. Rotation is subdivided into the number of states, n, using spherical linear interpolation (SLERP) of quaternions. SLERP has several advantages over linear interpolation: The shortest path between two angles is guaranteed; and the velocity of the object remains constant throughout the rotation.

Fast Finish:

A tooth-specific number of states, is computed for each tooth. For each tooth, tooth translation is subdivided into the number of states, by dividing the total translation amount evenly among states. Rotation is subdivided into the number of states, $n_i$, using SLERP. The interpolation for each tooth is subsequently zero-padded so that the total number of states is n.

Enabling Options for More Orthodontist Control and/or Hybrid Treatment

By controlling the constraints (and thus, resolution) in the interpolation parameters and/or staging thresholds, either a coarse or fine orthodontic correction can be accomplished. These constraints can be dictated by the amount of control an orthodontist would like to have in the treatment process. High resolution (small constraints) give an orthodontist greater ability to control and monitor the treatment as it progresses, since it results in a fine orthodontic correction that could imply more visits to the orthodontist office and smaller, more precise motions exerted by the clear tray aligners (CTAs). Low resolution (large constraints) provide less control, which could be desirable for less complex cases and to keep the costs low. This multiplicity of options can also translate to a hybrid treatment process. During the larger movement phase, traditional brackets and wires can be involved to result in a stage at which CTAs can take over.

Figure 8:
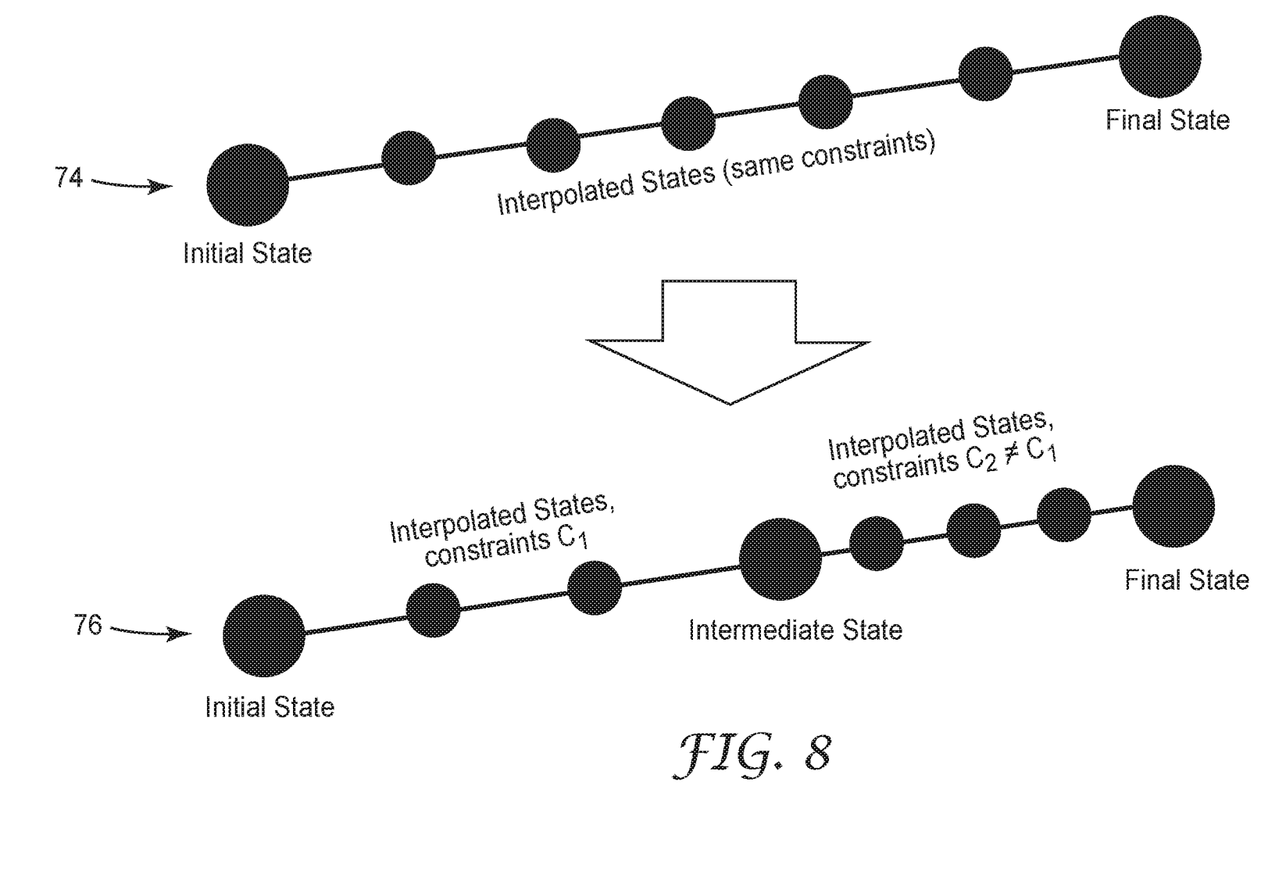
FIG. 8 is a diagram illustrating that interpolation between states for single set of constraints can be modified to incorporate different sets of constraints.

The method above could be adjusted to allow for forces that change throughout the course of treatment, as illustrated in FIG. 8, allowing for treatment planning with a set of different appliances (e.g., brackets and wires followed by clear tray aligners). To modify the forces, first define an intermediate state where treatment modality will be switched. Next, define the constraints on tooth movement from the initial state to the intermediate state (c1) and from the intermediate state to the final state, (c2), and perform interpolation.

FIG. 8 is a diagram illustrating that interpolation between states for single set of constraints 74 can be modified to incorporate different sets of constraints 76 due to, for example, a change in the corresponding treatment appliance.

This process is also applicable to CTAs made from different materials which have different inherent forces but at varying costs. This will allow orthodontists to communicate to the patient about different treatment options based on cost (material+time cost+office visits), treatment time, aesthetics (CTA time), and other factors.

The invention claimed is:

1. A computer-implemented method for automatically removing collisions between digital mesh objects, comprising steps of:
   receiving a set of digital mesh objects in a first state with one or more collisions between the digital mesh objects;
   determining one or more objects that are in a state of collision;
   determining one or more objects that are not in a state of collision and that neighbor the one or more objects that are in the state of collision;
   performing a perturbation method on the one or more neighboring objects with one or more first perturbation magnitudes;
   performing a perturbation method on the one or more objects in the state of collision with a second magnitude; and
   outputting a set of transformations describing tooth movement between the first state and a second state or tooth positions in the second state,
   wherein the tooth movement or the tooth positions are represented by the digital mesh objects.

2. The method of claim 1, wherein the perturbation method comprises using a directional perturbation method.

3. The method of claim 1, wherein the perturbation method comprises using a propagated directional perturbation method.

4. The method of claim 1, wherein the perturbation method comprises using a gradient descent method.

5. The method of claim 1, wherein the perturbation method comprises using a simultaneous perturbation stochastic approximation method.

6. The method of claim 1, wherein the perturbation method comprises using a grid search method.

7. The method of claim 1, wherein the perturbation method comprises using a behavior mode-based perturbation method.

8. The method of claim 1, wherein the perturbation method comprises using a genetic algorithm.

9. The method of claim 1, wherein the outputting step comprises outputting the set of digital mesh objects in the second state as a digital setup for dental or orthodontic treatment planning.

10. The method of claim 1, wherein the outputting step comprises outputting the set of transformations required to move teeth from the first state to the second state.

11. The method of claim 1, wherein the outputting step comprises outputting the set of digital mesh objects in the second state without collisions between the digital mesh objects.

12. The method of claim 1, wherein each one of the one or more first magnitudes is less than the second magnitude.

13. The method of claim 1, wherein each one of the one or more first magnitudes is determined, at least in part by, scaling a magnitude of perturbation according to the distance between the one or more colliding objects and the one or more neighboring objects, wherein the one or more first magnitudes are larger relative to another one of the one or more first magnitudes the closer the one or more neighboring objects are to the one or more colliding objects.

14. A system for automatically removing collisions between digital mesh objects comprising:
- at least one non-transitory computer-readable storage medium having computer program instructions stored thereon,
- at least one processor communicatively coupled to the at least one non-transitory computer-readable storage medium and configured to execute the instructions to:
- receive a set of digital mesh objects in a first state with one or more collisions between the digital mesh objects;
- determine one or more objects that are in a state of collision;
- determine one or more objects that are not in a state of collision and that neighbor the one or more objects that are in the state of collision;
- perform a perturbation method on the one or more neighboring objects with one or more first perturbation magnitudes;
- perform a perturbation method on the one or more objects in the state of collision with a second magnitude; and
- output a set of transformations describing tooth movement between the first state and a second state or tooth positions in the second state, wherein the tooth movement or the tooth positions are represented by the digital mesh objects.

15. The system of claim 14, wherein the perturbation method comprises using a directional perturbation method.

16. The system of claim 14, wherein the perturbation method comprises using a propagated directional perturbation method.

17. The system of claim 14, wherein the perturbation method comprises using a gradient descent method.

18. The system of claim 14, wherein the outputting step comprises outputting the set of digital mesh objects in the second state as a digital setup for dental or orthodontic treatment planning.

19. The system of claim 14, wherein the outputting step comprises outputting the set of transformations required to move teeth from the first state to the second state.

20. The system of claim 14, wherein the outputting step comprises outputting the set of digital mesh objects in the second state without collisions between the digital mesh objects.

* * * * *